United States Patent [19]

Albert et al.

[11] Patent Number: 5,650,134

[45] Date of Patent: Jul. 22, 1997

[54] PEPTIDES

[75] Inventors: Rainer Albert, Basel, Switzerland; Helmut Mäcke, Lörrach, Germany

[73] Assignee: Novartis AG (formerly Sandoz Ltd.), Basel, Switzerland

[21] Appl. No.: 501,328

[22] Filed: Jul. 12, 1995

Related U.S. Application Data

[63] Continuation-in-part of Ser. No. 375,098, Jan. 19, 1995, abandoned, which is a continuation of Ser. No. 180,576, Jan. 12, 1994, abandoned.

[30] Foreign Application Priority Data

Jan. 12, 1993 [GB] United Kingdom ............ 9300510
Jun. 24, 1993 [GB] United Kingdom ............ 9313129
Jul. 28, 1993 [GB] United Kingdom ............ 9315561

[51] Int. Cl.$^6$ .......................... A61K 51/00; A61M 36/14
[52] U.S. Cl. .................. 424/1.69; 530/328; 530/327; 530/300; 534/10; 534/14
[58] Field of Search .................. 424/1.69, 1.11, 424/1.65, 9.1; 534/10–16; 530/300, 324–330; 540/450

[56] References Cited

U.S. PATENT DOCUMENTS

| 4,678,667 | 7/1987 | Meares et al. | 424/1.11 |
|---|---|---|---|
| 4,849,207 | 7/1989 | Sakata et al. | |
| 5,006,643 | 4/1991 | Fazio et al. | 534/10 |
| 5,057,302 | 10/1991 | Johnson et al. | 424/1.11 |
| 5,112,953 | 5/1992 | Gustavson et al. | |
| 5,219,555 | 6/1993 | Bremer et al. | 534/10 |
| 5,428,154 | 6/1995 | Gansow et al. | 534/10 |

FOREIGN PATENT DOCUMENTS

| 0515313 | 11/1992 | European Pat. Off. |
|---|---|---|
| 0498771 | 12/1992 | European Pat. Off. |
| 0607103 | 7/1994 | European Pat. Off. |
| 2225579 | 6/1990 | United Kingdom |
| 2241167 | 8/1991 | United Kingdom |

OTHER PUBLICATIONS

Kline et al (1991). Bioconjugate Chemistry, vol. 2, pp. 26–31. Carboxymethyl–Substituted Bifunctional Chelators: Preparation of Aryl Isothiocyanate Derivatives of 3–(carboxymethyl) 3–a zapentanedioic acid, 3,12–bis(carboxymethyl)–6,9–dioxa–3,12–diazatetradecanedioic Acid, and 1,4,7,10–Tetraazacyclodedecane–N,N',N",N"'–tetraacetic Acid for Us a Protein Labels.

Lewis et al (1994) Bioconjugate Chemistry, vol. 5, No. 6 pp. 565–576. A Facile, Water Soluble Method for Modification of Proteins with DOTA.

Holum (1991) Elements of General, Organic, and Biological Chemistry pp. 42–47.

Improved in Vivo Stability and Tumor Targeting of Bismuth–labeled Antibody Cancer Research 50, 4221–4226, Jul. 15, 1990.

J. Org. Chem., vol. 58, No. 24, 1993 pp. 6895–6899.

Chemical Abstracts—vol. 118, 1993; 255354r.

Radiolabeled Octreotide—S. J. Mather, et al. Cell Biophysics—vol. 21, 1992—pp. 93–107.

*Primary Examiner*—John Kight
*Assistant Examiner*—Dameron L. Jones
*Attorney, Agent, or Firm*—Robert S. Honor; Melvyn M. Kassenoff; Thomas O. McGovern

[57] ABSTRACT

Somatostatin peptides bearing a chelating group selected from a bifunctional $N_4$-chelating group particularly suitable for Tc, Rh, Cu, Co or Re-labelling, and a bifunctional polyamino-polycarboxylic acid chelating group are complexed with a α-, β-, γ- or positron-emitting nuclide or a nuclide with Auger-e$^-$-cascades and are useful as radiopharmaceuticals.

21 Claims, No Drawings

PEPTIDES

The present application is a continuation-in-part of previously filed application Ser. No. 08/375,098, filed Jan. 19, 1995, now abandoned, which is a continuation of Ser. No. 08/180,576, filed Jan. 12, 1994, abandoned.

The present invention relates to polypeptides, process for their production, pharmaceutical preparations containing them and their use as a pharmaceutical, e.g. for treatment of somatostatin receptor positive tumors or as in vivo diagnostic imaging agents.

GB-A-2,225,579 discloses somatostatin peptides bearing at least one chelating group which can be labelled for in vivo diagnostic and therapeutic applications. These compounds are capable of binding to somatostatin receptors, e.g. expressed or overexpressed by tumor or metastases.

The present invention provides new somatostatin peptide ligands bearing at least one chelating group selected from a bifunctional $N_4$-chelating group particularly suitable for Tc, Rh, Cu, Co or Re-labelling and a bifunctional polyamino-polycarboxylic acid chelating group, particularly adapted for In or Y-labelling, the chelating group being attached to an amino group which does not significantly interfere with or prevent receptor binding of the thus modified peptide. The chelating group may be attached either directly or indirectly through a spacer group to the somatostatin peptide.

According to the invention there is provided a compound of formula I $$X-HN-P \qquad \qquad I$$

wherein

X is a radical selected from
a) a chelating group of formula $X_1$

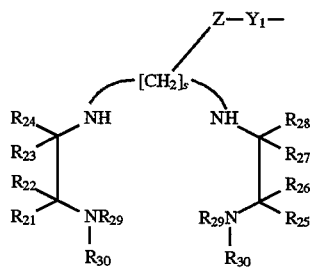

$$(X_1)$$

wherein each of $R_{21}$ to $R_{28}$ independently is hydrogen, $C_{1-6}$ alkyl or hydroxy substituted $C_{1-6}$alkyl, one of $R_{29}$ and $R_{30}$ is hydrogen, $C_{1-6}$ alkyl or an amino protecting group and the other is hydrogen or $C_{1-4}$ alkyl s is 2, 3 or 4, Z is a divalent group, and $Y_1$ is a single bond or a spacer group, and b) a radical of formula $X_2$

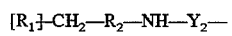

$$(X_2)$$

wherein $R_1$ is a bifunctional chelating group derived from a polyamino-polycarboxylic acid or anhydride and bearing the moiety $-CH_2-R_2-NH-Y_2$ on a tertiary carbon atom, $R_2$ is $C_{1-3}$alkylene or optionally substituted phenylene, and $Y_2$ is $-CO-$ or a spacer group comprising on one end a $-CO-$ and on the other end a $-CH_2-$ group or a $-CO-$ at each end, P—NH— is the N-terminal residue of a somatostatin peptide of formula P—$NH_2$.

These compounds are referred to thereafter as LIGANDS OF THE INVENTION.

The term "somatostatin peptide" includes the naturally occurring somatostatin (tetradecapeptide) and its analogues or derivatives.

By derivatives or analogues as used herein is meant any straight-chain or cyclic polypeptide derived from that of the naturally occurring tetradecapeptide somatostatin wherein one or more amino acid units have been omitted and/or replaced by one or more other amino acid radical(s) and/or wherein one or more functional groups have been replaced by one or more other functional groups and/or one or more groups have been replaced by one or several other isosteric groups. In general, the term covers all modified derivatives or analogues of the naturally occurring somatostatin peptide which exhibit a qualitatively similar effect to that of the unmodified somatostatin peptide, e.g. they bind to somatostatin receptors.

Cyclic, bridge cyclic and straight-chain somatostatin analogues are known compounds. Such compounds and their preparation are described in European Patent 29,579; 215, 171; 203,031; and 214,872.

Preferred LIGANDS OF THE INVENTION are compounds of formula I wherein P—NH— is a residue of formula (a)

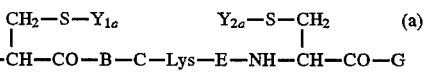

$$(a)$$

wherein

R is
 a) an L- or D-phenylalanine residue optionally ring-substituted by F, Cl, Br, $NO_2$, $NH_2$, OH, $C_{1-3}$alkyl and/or $C_{1-3}$alkoxy;
 b) the residue of a natural or non natural α-amino acid other than defined under a) above or of a corresponding D-amino acid, or
 c) a dipeptide residue in which the individual amino acid residues are the same or different and are selected from those defined under a) and/or b) above, $Y_{1a}$ and $Y_{2a}$ represent together a direct bond or each of $Y_{1a}$ and $Y_{2a}$ is independently hydrogen, B is -Phe- optionally ring-substituted by halogen, $NO_2$, $NH_2$, OH, $C_{1-3}$alkyl and/or $C_{1-3}$alkoxy (including pentafluoroalanine), or β-naphthyl-Ala C is (L)-Trp- or (D)-Trp- optionally α-N-methylated and optionally benzene-ring-substituted by halogen, $NO_2$, $NH_2$, OH, $C_{1-3}$alkyl and/or $C_{1-3}$ alkoxy, E is Thr, Ser, Val, Phe, Ile or an aminoisobutyric or aminobutyric acid residue G is a group of formula

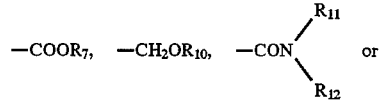

-continued

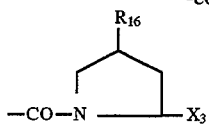

wherein $R_7$ is hydrogen or $C_{1-3}$alkyl, $R_{10}$ is hydrogen or the residue of a physiologically acceptable, physiologically hydrolysable ester, $R_{11}$ is hydrogen, $C_{1-3}$alkyl, phenyl or $C_{7-10}$phenylalkyl, $R_{12}$ is hydrogen, $C_{1-3}$alkyl or a group of formula —CH($R_{13}$)—$X_3$, $R_{13}$ is —CH$_2$OH, —(CH$_2$)$_2$—OH, —(CH$_2$)$_3$—OH, or —CH(CH$_3$)OH or represents the substituent attached to the α-carbon atom of a natural or non natural α-amino acid (including hydrogen) and $X_3$ is a group of formula —COOR$_7$, —CH$_2$OR$_{10}$ or

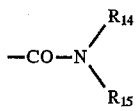

wherein $R_7$ and $R_{10}$ have the meanings given above, $R_{14}$ is hydrogen or $C_{1-3}$alkyl and $R_{15}$ is hydrogen, $C_{1-3}$alkyl, phenyl or $C_{7-10}$phenylalkyl, and $R_{16}$ is hydrogen or hydroxy, with the proviso that when $R_{12}$ is —CH($R_{13}$)—$X_3$ then $R_{11}$ is hydrogen or methyl, wherein the residues B and E have the L-configuration, and the residues in the 2-and 7-position have the (L)- or (D)-configuration.

Halogen is preferably fluorine, chlorine or iodine, more preferably fluorine.

In the residue of formula (a), the following significances are preferred either individually or in any combination or sub-combination:

1.1. When R has the meaning a) this is preferably a') an L- or D-phenylalanine or -tyrosine residue. More preferably a') is an L- or D-phenylalanine residue.

1.2. When R has the meaning b) or c) the defined residue is preferably lipophilic. Preferred residues b) thus b') are α-amino acid residues having a hydrocarbon side chain, e.g. alkyl with 3, preferably 4, or more C atoms, e.g. up to 7 C-atoms, or a naphthyl-methyl or heteroaryl side chain, e.g. pyridyl-methyl or indol-3-yl-methyl, said residues having the L- or D-configuration. Preferred residues c) are dipeptide residues in which the individual amino acid residues are the same or different and are selected from those defined under a') and b') above.

1.3. Most preferably R has the meaning a) especially the meaning a').

2. B is B', where B' is Phe or Tyr.

3. C is C', where C' is (D)Trp.

4. E is E' where E' is Ser, Val or Thr, especially Thr

5. G is G', where G' is a group of formula

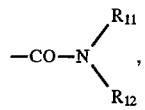

especially a group of formula

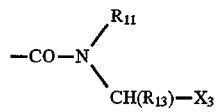

(in which case $R_{11}$=H or CH$_3$). In the latter case the moiety —CH($R_{13}$)—$X_3$ preferably has the L-configuration.

6.1. $R_{11}$ is preferably hydrogen.

6.2. As the substituent attached to the α-carbon atom of a natural or non natural amino acid (i.e. of formula H$_2$N—CH($R_{13}$)—COOH), $R_{13}$ is preferably —CH$_2$OH, —CH(CH$_3$)—OH, —(CH$_2$)$_2$OH, —(CH$_2$)$_3$—OH, isobutyl, butyl, naphthyl-methyl or indol-3-yl-methyl. It is especially —CH$_2$OH or —CH(CH$_3$)OH—.

6.3. $X_3$ is preferably a group of formula

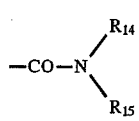

or —CH$_2$—OR$_{10}$, especially of formula —CH$_2$—OR$_{10}$ and $R_{10}$ is preferably hydrogen or as an ester residue formyl, $C_{2-12}$ alkylcarbonyl, $C_{8-12}$ phenylalkylcarbonyl or benzoyl. Most preferably $R_{10}$ is hydrogen.

7. Preferably $Y_{1a}$ and $Y_{2a}$ together represent a direct bond.

The following residues are illustrative for the residue of formula (a):

-(D)Phe-Cys-Phe-(D)Trp-Lys-Thr-Cys-Thr-ol

-(D)Phe-Cys-Tyr-(D)Trp-Lys-Val-Cys-ThrNH$_2$

-(D)Phe-Cys-Tyr-(D)Trp-Lys-Val-Cys-TrpNH$_2$

-(D)Trp-Cys-Phe-(D)Trp-Lys-Thr-Cys-ThrNH$_2$

-(D)Phe-Cys-Phe-(D)Trp-Lys-Thr-Cys-ThrNH$_2$

-3-(2-Naphthyl)-(D)Ala-Cys-Tyr-(D)Trp-Lys-Val-Cys-ThrNH$_2$

-3-(2-Naphthyl)-(D)Ala-Cys-Tyr-(D)Trp-Lys-Val-Cys-β-Nal-NH$_2$

-3-(2-Naphthyl)-(D)Ala-Cys-β-Nal-(D)Trp-Lys-Val-Cys-ThrNH$_2$

-(D)Phe-Cys-Phe-(D)Trp-Lys-Thr-Cys-β-Nal-NH$_2$

Further preferred LIGANDS OF THE INVENTION are compounds of formula I wherein P—NH— is a residue of formula (b) or c)

| | |
|---|---|
| -Cys-Phe-Phe-(D)-Trp-Lys-Thr-Phe-Cys-ol | (b) |
| -Cys-His-His-Phe-Phe-(D)Trp-Lys-Thr-Phe-Thr-Ser-Cys-OH | (c) |

It is understood that —Z—Y$_1$ is attached to one of the carbon atom of —[CH$_2$]$_s$ in replacement of an hydrogen atom.

In the radical of formula $X_1$, $C_{1-6}$alkyl as any of $R_{21}$ to $R_{28}$ is preferably $C_{1-3}$alkyl, particularly methyl. Hydroxy substituted $C_{1-6}$alkyl is preferably hydroxy substituted $C_{1-3}$alkyl, particularly —$CH_2OH$ or —$CH_2CH_2$—OH. Most preferably any of $R_{21}$ to $R_{30}$ is H.

Examples of protecting groups as $R_{30}$ are e.g. disclosed in "Protective Groups in Organic Synthesis", T. W. Greene, J. Wiley & Sons NY (1981), 219–287, for example acyl such as acetyl, methoxysuccinyl, hydroxysuccinyl or benzoyl optionally substituted on the phenyl ring with e.g. p-methoxycarbonyl, p-methoxy or p-nitro; alkoxycarbonyl such as t-butyloxycarbonyl; arylmethoxycarbonyl such as 9-fluorenylmethoxycarbonyl or benzyloxy carbonyl optionally substituted on the phenyl ring with p-methoxy, p-nitro, p-chloro or m-phenyl; arylmethyl such as benzyl optionally ring substituted with p-methoxy, p-nitro or p-chloro; or arylsulfonyl such as phenylsulfonyl optionally ring substituted with p-methyl or p-methoxy, or naphthylsulfonyl optionally ring substituted with e.g. amino or di($C_{1-4}$alkyl) amino.

Preferably one of $R_{29}$ and $R_{30}$ is H or $CH_3$, more preferably $R_{29}$ and $R_{30}$ are each H.

Examples of Z include radicals of formula —$(Z_1)_t$—$Z_2$ wherein $Z_1$ is $C_{1-6}$alkylene; $C_{1-6}$alkylene attached to the carbon atom by an oxygen atom or —NH—; or $(CH_2)_k$—O— wherein k is 0, 1, 2 or 3; t is 0 or 1 and $Z_2$ is derived from a group capable of reacting with the terminal amino group of a somatostatin peptide, when $Y_1$ is a single bond or with a $Y_1$-yielding compound when $Y_1$ is a spacer group e.g. —NCS or a carboxy group or a functional derivative thereof, e.g. acid halide, anhydride or hydrazide.

Z is preferably a group derived from

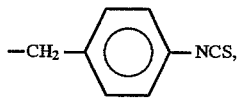

particularly when $Y_1$ is a single bond.

Examples of $Y_1$ as a spacer group include e.g. a radical of formula (b)

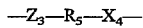

(b)

wherein
$Z_3$ is a divalent group derived from a functional moiety capable of covalently reacting with a functional moiety from which Z is derived,
$X_4$ is a divalent group derived from a functional moiety capable of covalently reacting with the terminal amino group of a somatostatin peptide, and
$R_5$ is $C_{1-6}$alkylene optionally interrupted by one or more heteroatoms or radicals selected from oxygen, sulfur, CO, —NHCO—, N($C_{1-4}$alkyl)—CO—, —NH— and —N($C_{1-4}$alkyl)—; hydroxy substituted $C_{1-6}$alkylene; $C_{2-6}$alkenylene; optionally substituted cycloalkylene;

or a radical of formula ($\alpha_1$)

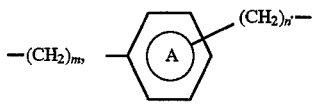

($\alpha_1$)

wherein
each of m' and n' independently is 0, 1, 2 or 3, the ring A is optionally substituted and $R_6$ is a residue as attached in $C_\alpha$ of a natural or non natural α-amino acid.

Example of $R_6$ include e.g. the residue attached in $C_\alpha$ of Ala, Leu, Ile, Val, Nle, Lys or Orn.

When $R_5$ is substituted cycloalkylene or is or comprises a substituted ring A, it is preferably substituted by up to 3 substituents selected from halogen, hydroxy, $C_{1-3}$alkyl and $C_{1-3}$alkoxy. Preferably the cycloalkylene moiety or the ring A is unsubstituted.

Each of $Z_3$ and $X_4$, independently, may be for example —CO— or —CS—. $Z_3$ may also be e.g. —NH—. A suitable example for the radical of formula (b) is e.g. succinyl, β-Ala or a divalent residue derived from 6-amino-caproic acid. Preferably $Y_1$ is a single bond.

In the radical of formula $X_2$, $R_1$ is preferably a bifunctional chelating group derived from a polyamino polyacetic acid or anhydride, e.g. diethylene triamine pentaacetic acid (DTPA), a macrocyclic compound such as 1,4,7,10-tetraazacyclododecane-N,N',N'',N'''-tetraacetic acid (DOTA), 1,4,8,11-tetraazacyclotetradecane-N,N',N'',N'''-tetraacetic acid (TETA) or 1,4,7,10-tetraazacyclotridecane-N,N',N'',N'''-tetraacetic acid (TRITA). In addition to the —$CH_2$—$R_2$—NH—$Y_2$ moiety, $R_1$ may be further substituted, e.g. by $C_{1-3}$alkyl.

More preferably $R_1$ is a chelating group derived from DTPA, 4-methyl-DTPA or DOTA.

When $R_2$ is substituted phenylene, it may bear up to three substituents selected from halogen, hydroxy, $C_{1-3}$alkyl and $C_{1-3}$alkoxy. Preferably $R_2$ is unsubstituted phenylene.

When $Y_2$ is a spacer group as indicated above, it may be e.g. —CO—$CH_2$—, —CO—$(CH_2)_2$—, —$CH_2$—CO—, —$(CH_2)_2$—CO— or a radical of formula (b')

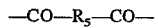

(b')

wherein $R_5$ is as defined above.

A suitable example for the residue of formula (b') is the dicarbonyl residue of a dicarboxylic acid, e.g. succinyl.

The LIGANDS OF THE INVENTION may exist e.g. in free or salt form. Salts include acid addition salts with e.g. organic acids, polymeric acids or inorganic acids, for example hydrochlorides and acetates.

The present invention also includes a process for the production of the LIGANDS OF THE INVENTION. They may be produced by analogy to known methods.

The LIGANDS OF THE INVENTION may be produced for example as follows:
a) removing at least one protecting group which is present in a compound of formula I in protected form, or
b) linking together by an amide bond two peptide units, each of them containing at least one amino acid or amino alcohol in protected or unprotected form and one of them containing a radical X, wherein the amide bond is in such a way that the desired amino acid sequence is obtained, and stage a) of the process is then optionally effected, or
c) linking together a chelating agent bearing optionally a functional moiety capable of yielding $Y_2$ or the spacer group $Y_1$, and the desired somatostatin peptide in protected or unprotected form in such a way that the radical X is fixed on the terminal amino group of the peptide, and stage a) is then optionally effected or,
d) linking together a chelating agent and the desired somatostatin peptide in protected or unprotected form, the peptide bearing on its terminal amino group a functional moiety capable of yielding $Y_2$ or the spacer group $Y_1$, in such a way that the radical X is fixed on the terminal amino group of the peptide, and stage a) is then optionally effected, or
e) removing a functional group of an unprotected or a protected peptide bearing a radical X or converting it into another functional group so that an other unprotected or protected compound of formula I is obtained and in the latter case stage a) of the process is effected,
and recovering the LIGAND thus obtained in free form or in salt form.

The above reactions may be effected in analogy with known methods, e.g. as described in the following examples. Where desired, in these reactions, protecting groups which are suitable for use in peptides or for the desired chelating groups may be used for functional groups which do not participate in the reaction. The term protecting group may also include a polymer resin having functional groups.

The peptide fragment bearing the radical X and used in stage b) may be prepared by reacting the peptide fragment comprising at least one amino acid in protected or unprotected form with a chelating agent as indicated in process step c) or d).

The somatostatin peptide or fragment or the amino acid bearing functional moiety capable of yielding $Y_2$ or $Y_1$ and used as starting material in process step b) or d) may be prepared by reacting the peptide, fragment or amino acid with a $Y_2$- or $Y_1$-yielding compound e.g. an ω-amino carboxylic acid, a dicarboxylic acid or an ω-formyl carboxylic acid, for example $NH_2$—$R_5$—COOH, succinic acid, adipic acid, glyoxylic acid or a functional derivative thereof.

The chelating agent bearing a functional moiety capable of yielding $Y_2$ or $Y_1$ used as starting material in process step b) or c) may be prepared by reacting the chelating agent with a $Y_2$- or $Y_1$-yielding compound, e.g. as indicated above.

Compounds wherein $Y_2$ is —CO— can be prepared using starting materials obtained by reaction with phosgene.

By functional derivatives of a carboxylic or dicarboxylic acid are meant e.g. anhydrides, acid halogenides, esters etc. . . . .

In accordance with process step e), for example a compound of formula I wherein each of $Y_1$ and $Y_2$ is H can be oxidized into compound of formula I wherein $Y_1$ and $Y_2$ form together a direct bond.

The LIGANDS OF THE INVENTION in free form or in the form of pharmaceutically acceptable salts are valuable compounds. According to a further embodiment, the LIGANDS OF THE INVENTION can be complexed with a nuclide, e.g. a γ-, a positron-, α- or β-emitting nuclide or nuclides with Auger-e⁻-cascades.

Accordingly, the present invention also provides the LIGANDS OF THE INVENTION as defined above which are complexed with a nuclide (hereinafter referred to a CHELATES OF THE INVENTION), in free form or in salt form, their preparation and their use for in vivo diagnostic and therapeutic treatment.

LIGANDS of formula I wherein X is a chelating group of formula $X_1$ are preferably complexed with a Tc, Rh, Cu, Co or Re isotope, e.g. $^{99m}$Tc, $^{186}$Re, $^{188}$Re, $^{105}$Rh, $^{57}$Co, $^{64}$Cu or $^{67}$Cu, preferably $^{99m}$Tc. LIGANDS of formula I wherein X is a chelating group of formula $X_2$ are preferably complexed with a radiolanthanide, particularly $^{111}$In, $^{90}$Y, $^{140}$La, $^{161}$Tb, $^{169}$Er, $^{212}$Bi, $^{153}$Sm, $^{64}$Cu, $^{67}$Cu, $^{211}$At, $^{111}$Ag, $^{32}$P, $^{51}$Cr, $^{67}$Ga, $^{71}$Ge, $^{169}$Yb, more preferably a α- or β-emitting nuclide, most preferably $^{90}$Y.

The CHELATES OF THE INVENTION may be prepared by reacting the LIGAND with a corresponding nuclide yielding compound, e.g. a metal salt, preferably a water-soluble salt. The reaction may be carried out by analogy with known methods, e.g. as disclosed by D. E. Trontner, W. A. Valket, T. J. Hoffmann et al., Int. J. Appl. Radiat. Isot. 1984, 35(6), 467–70. $^{99m}$Tc may be used in oxidized form, e.g. $^{99m}$Tc-pertechnate, which may be complexed under reducing conditions.

Preferably the complexing of the LIGAND is effected at a pH at which the LIGAND OF THE INVENTION is stable.

Alternatively the nuclide may also be provided to the solution as a complex with an intermediate chelating agent, e.g. a chelating agent which forms a chelate complex that renders the nuclide soluble at the physiological pH of the LIGAND but is less thermodynamically stable than the CHELATE. Example of such an intermediate chelating agents are 4,5-dihydroxy-1, 3-benzenedisulfonic acid (Tiron), citrate, tartarate, glucoheptonate. In such a process, the nuclide exchanges the ligand.

The present invention also provides a process for labelling with a β-emitting rare earth radionuclide, e.g. β-emitting Y, Tb or Sm, e.g. $^{90}$Y, a peptide ligand comprising a bifunctional chelating group derived from a macrocyclic polyamino polyacetic acid compound such as DOTA, TETA or TRITA and attached through a spacer group, e.g. —CO—$CH_2$—, —CO—$(CH_2)_2$—, —$CH_2$CO—, —$(CH_2)_2$—CO—, or a radical of formula (b'), to an amino group of the peptide, e.g. the terminal amino group, which process comprises reacting said peptide ligand with a β-emitting rare earth radionuclide-yielding compound, e.g. a rare earth radionuclide salt, at a temperature from 60° to 120° C., preferably from 90° to 100° C.

The labelling under heating may conveniently be carried out during a time period of 10 to 20 minutes. The heating may be performed in an autoclave when the temperature is ≧100° C. Rare earth radionuclide salts include e.g. chlorides, for example $YCl_3$. Examples of peptide ligands are e.g. somatostatin, insulin, EGF peptide ligands, e.g. a compound of formula I wherein X is a radical of formula $X_2$ wherein $R_1$ is a bifunctional chelating group derived from a macrocyclic polyamino polyacetic acid compound such as DOTA, TETA or TRITA. The labelling of a compound of formula I as mentioned, preferably wherein X is a radical of formula $X_2$ wherein $R_1$ is a bifunctional chelating group derived from DOTA, e.g. the compound of Example 7 or 8, is preferably performed at a temperature from 60° to 120° C., more preferably from 90° to 100° C., particularly as disclosed in Example 12. CHELATES with a high radiolabelled purity, e.g. >99.5% are obtained.

The labelling at a temperature of from 60° to 120° C. improves the levels of radionuclide incorporation, particularly of $^{90}$Y incorporation. The short reaction time and the lack of a further chemical purification step (no separation of chelated and unchelated radionuclide is required) produce a high specific activity product which is substantially not decomposed by autoradiolysis.

The above mentioned reactions may conveniently be effected under conditions avoiding trace metal contamination. Preferably distilled de-ionized water, ultrapure reagents, no carrier-added radioactivity etc. are used to reduce the effects of trace metal.

The CHELATES OF THE INVENTION may exist e.g. in free or salt form. Salts include acid addition salts with e.g. organic acids, polymeric acids or inorganic acids, for example hydrochlorides and acetates.

The CHELATES OF THE INVENTION and their pharmaceutical acceptable salts exhibit pharmaceutical activity and are therefore useful either as an imaging agent, e.g. visualisation of somatostatin receptor accumulation e.g. somatostatin receptor positive tumors and metastases, inflammatory or autoimmune disorders exhibiting somatostatin receptors, tuberculosis or organ rejection after transplantation, when complexed with a γ- or positron-emitting nuclide, e.g. $^{111}$In, $^{99m}$Tc or $^{68}$Ga, or as a radiopharmaceutical for the treatment in vivo of somatostatin receptor positive tumors and metastases when complexed with an α- or β-emitting nuclide, or a nuclide with Auger-e⁻-cascades, e.g. $^{90}$Y, $^{186}$Re or $^{188}$Re as indicated by standard tests.

In particular, the LIGANDS OF THE INVENTION and the CHELATES OF THE INVENTION possess affinity for somatostatin receptors which can be assessed in binding assays performed as disclosed by J. C. Reubi, Life Sc. 36, 1829 (1985) and by C. Bruns et al. in Biochem. J., 265, 39 (1990).

It is observed that the CHELATES OF THE INVENTION, e.g. a $^{111}$In, $^{88}$Y, $^{90}$Y or $^{99m}$Tc CHELATE, binds with a good affinity to somatostatin receptors with pKi values of from about 8 to 11. The compound of Example 2 has a pKi$_{50}$ value of 9.4 and compounds of Examples 9 and 10 have a pKi$_{50}$ value of 9.0 and 8.9 respectively.

The affinity of the CHELATES OF THE INVENTION for somatostatin receptors can also be shown by in vivo testing, according to standard test methods, e.g. as disclosed in GB-A-2, 225,579. For example the compound of Example 2 gives a tumor accumulation of 1.9±0.4% injected dose per g (n=6) 4 hours after injection into rats bearing an exocrine pancreatic tumor.

After administration of a CHELATE OF THE INVENTION, e.g. a $^{111}$In, $^{86}$Y or $^{99m}$Tc CHELATE, at a dosage of from 1 to 5 µg/kg of LIGAND labelled with 0.1 to 5 mCi nuclide, preferably 0.1 to 2 mCi the tumor site becomes detectable together with the organs where excretion essentially takes place. The CHELATES particularly wherein X is X$_2$ have a high serum stability and a high accumulation in tumorous tissues compared to normal organs.

Accordingly, in a series of specific or alternative embodiments, the present invention also provides:

1. A method for in vivo detection of somatostatin receptor accumulation in a subject which comprises a) administering a CHELATE OF THE INVENTION to said subject and b) recording the localisation of the receptors targeted by said CHELATE.

CHELATES OF THE INVENTION for use in the in vivo detection method of the invention are the CHELATES which are complexed with a γ- or positron-emitting nuclide, particularly a Tc, Re, In or Cu, more preferably $^{99m}$Tc, $^{111}$In or $^{86}$Y.

The CHELATES OF THE INVENTION for use as an imaging agent in method (1) may be administered intraperitoneally, preferably intravenously, e.g. in the form of injectable solutions or suspensions, preferably in a single injection. The appropriate dosage will of course vary depending upon, for example, the LIGAND. A suitable dose to be injected is in the range to enable imaging by photoscanning procedures known in the art.

A CHELATE OF THE INVENTION may advantageously be administered in a dose comprising 0.1 to 50 mCi of a stably chelated nuclide, preferably 0.1 to 30 mCi; more preferably it is 2 to 30 mCi per µMol LIGAND, particularly when the nuclide is $^{99m}$Tc. With $^{111}$In or $^{86}$Y, the CHELATE may be administered in a dose of 0.1 to 10 mCi.

In animals an indicated dosage range may be of from 0.1 to 10 µg/kg of a CHELATE labelled with 0.5 to 2 mCi γ-emitting nuclide, preferably when X is a chelating group X$_1$ and the nuclide is $^{99m}$Tc, or from 0.01 to 1 µg/kg of a CHELATE labelled with 0.02 to 0.5 mCi γ-emitting nuclide, preferably when X is a chelating group X$_2$ and the nuclide is $^{111}$In or $^{86}$Y. In larger mammals, for example humans, an indicated dosage range may be of from 1 to 200 µg CHELATE, e.g. wherein X is X$_1$, labelled e.g. with 2 to 30 mCi $^{99m}$Tc, or from 1 to 20 µg CHELATE, e.g. wherein X is X$_2$, labelled e.g. with 1 to 10 mCi $^{111}$In or Y.

The enrichment with the CHELATES at the somatostatin receptor accumulation site may be followed by the corresponding imaging techniques, e.g. using nuclear medicine imaging instrumentation, for example a scanner, γ-camera, rotating γ-camera, PET, each preferably computer assisted. CHELATES OF THE INVENTION can also be useful in radioguided surgery of somatostatin receptor positive tumors, particularly the Tb CHELATES.

The In or Tc CHELATES OF THE INVENTION are substantially excreted through the kidneys.

2. A method for in vivo treatment of somatostatin receptor positive tumors and metastases in a subject in need of such a treatment which comprises administering to said subject a therapeutically effective amount of a CHELATE OF THE INVENTION.

CHELATES OF THE INVENTION for use in the in vivo treatment method of the invention are the CHELATES complexed with a α- or β-emitting nuclide or a nuclide with Auger-e⁻-cascades, e.g. as disclosed above, preferably $^{90}$Y.

Dosages employed in practising the therapeutic method of the present invention will of course vary depending e.g. on the particular condition to be treated, for example the volume of the tumor, the particular CHELATE employed, and the therapy desired. In general, the dose is calculated on the basis of radioactivity distribution to each organ and on observed target uptake. A β-emitting CHELATE may be administered at several time points over a period of 1 to 3 weeks. A single dosage may be of from 0.1 to 20 µg CHELATE, e.g. wherein X is X$_2$, labelled with 10 to 40 mCi of e.g. $^{90}$Y.

In animals an indicated dosage range may be of from 0.01 to 1 µg/kg of CHELATE wherein X is X$_2$ labelled with 0.1 to 1 mCi $^{90}$Y, or from 0.1 to 5 µg/kg of a CHELATE wherein X is X$_1$ labelled with 0.05 to 0.5 mCi Re. In larger mammals, for example humans, an indicated dosage range is of from 0.1 to 20 µg CHELATE wherein X is X$_2$ labelled with e.g. 10 to 40 mCi $^{90}$Y, or from 1 to 200 µg CHELATE wherein X is X$_1$ labelled with e.g. 0.1 to 1.5 mCi Re.

The CHELATES OF THE INVENTION for use in method (2) may be administered by any conventional route, in particular intraperitoneally or intravenously, e.g. in the form of injectable solutions or suspensions. They may also be administered advantageously by infusion, e.g. an infusion of 30 to 60 min. Depending on the site of the tumor, they may be administered as close as possible to the tumor site, e.g. by means of a catheter. The mode of administration selected may depend on the pharmacokinetic behaviour of the CHELATE used and the execretion rate.

The CHELATES OF THE INVENTION may be administered in free form or in pharmaceutically acceptable form. Such salts may be prepared in conventional manner and exhibit the same order of activity as the free compounds.

The CHELATES OF THE INVENTION for use in the method of the present invention may preferably be prepared shortly (i.e. the radiolabelling with the desired nuclide) before the administration to a subject.

The CHELATES OF THE INVENTION may be suitable for imaging or treating tumors such as pituitary, gastroenteropancreatic, central nervous system, breast, prostatic, ovarian or colonic tumours, small cell lung cancer, paragangliomas, kidney cancer, skin cancer, neuroblastomas, pheochromocytomas, medullary thyroid carcinomas, myelomas, lymphomas, Hodgking and non-Hodgkins disease, bone tumours and metastases thereof.

According to a further aspect of the invention, there is provided a pharmaceutical composition comprising a LIGAND or a CHELATE OF THE INVENTION in free or in pharmaceutically acceptable salt form, together with one or more pharmaceutically acceptable carriers or diluents therefor. Such compositions may be manufactured in conventional manner.

A composition according to the invention may also be presented in separate packages with instructions for mixing the LIGAND with the desired nuclide and for the administration of the resulting CHELATE. It may also be presented in twin-pack form, that is, as a single package containing separate unit dosages of the LIGAND and the desired nuclide with instructions for mixing them and for administration of the CHELATE. A diluent or carrier may be present in the unit dosage forms.

In the following examples, all temperatures are in °C and $[\alpha]_D^{20-}$ values uncorrected. The following abbreviations are employed:

| | |
|---|---|
| DMF | dimethyl formamide |
| Boc | tert.-butoxycarbonyl |
| TFA | trifluoroacetic acid |
| Fmoc | 9-fluorenylmethoxycarbonyl |
| AcOH | acetic acid |
| HOBT | 1-hydroxybenzotriazole |

Octreotide HDPhe—Cys—Phe—DTrp—Lys—Thr—Cys—Thr-ol

EXAMPLE 1

6-(p-isothiocyanatobenzyl)-1,4,8,11-tetraazaundecyl-

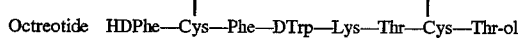
DPhe—Cys—Phe—DTrp—Lys—Thr—Cys—Thr-ol a) 515-mg

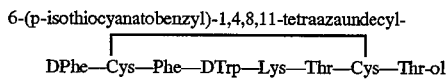
(415 μmole)ε-Fmoc—DPhe—Cys—Phe—DTrp—Lys—Thr—Cys—Thr-ol and 2 drops triethylamin are added to a solution of 595 mg (497 μmole)Fmoc-6-(p-isothiocyanatobenzyl)-1,4,8,11-tetraazaun deca-ne. After stirring at room temperature for 24 hours, the yellow suspension is chromatographied on silica gel using CHCl3/CH$_3$OH 97:3 as an eluant. Lyophilization yields a colourless solid.

MS (FAB) m/z (relative intensity): 2439 (MH$^+$,25), 1343 (100). Rf. 0,42 (SiO$_2$, CHCl$_3$/CH$_3$OH 9:1).

b) 10 ml piperidine/DMF (1:4 v/v) are added to 530 mg (217 μmole) of the compound obtained above and the mixture is kept at room temperature for 45 minutes. After removal of the solvent and base by distillation under high vacuo, the residue is chromatographied on silica gel. The impurities are removed with CHCl$_3$/CH$_3$OH/AcOH/H$_2$O 7:4:1:1 and the unprotected compound is eluted with CHCl$_3$/CH$_3$OH/AcOH 5:8:3. After desalting through HPLC on a Spherisorb column of 5 μm (Solution A: 1000 ml H$_2$O/l ml TFA; Solution B: 200 ml H$_2$O/800 ml CH$_3$CN/l ml TFA; linear gradiant from 95% solution A to 5% solution A within 20 minutes) and lyophilization, the title compound is obtained in the form of a colourless TFA-salt.

MS (FAB) m/z (relative intensity): 1326 (M$^+$, 18), 872 (100) Rf 0.41 (SiO$_2$, CHCl$_3$/CH$_3$OH/AcOH 5:8:3)

6-(p-Isothiocyanatobenzyl)-1,4,8,11-tetraazaundecane used as starting material may be prepared as follows:

a) 6-(p-nitrobenzyl)-1,4,8,11-tetraaza-5,7-dioxo-undecane 2 g freshly distilled ethylene diamine is added in one portion to a solution of 0.5 g diethyl p-nitrobenzyl-malonate in 50 ml CH$_3$OH and the mixture is heated to reflux at 80°. After 12 hours the mixture is allowed to cool to room temperature. The resulting turbid pale yellow mixture is placed in the refrigerator for crystallisation. The residue is filtered off. Purification is performed through middle pressure chromatography using silica gel and isopropanol/25% ammonium hydroxide 8:2 as mobile phase. The fractions with a Rf 0.34 are collected. After evaporation, there is obtained the title a) compound as a white yellowish solid.

FAB-MS (matrix:thioglycerine) MH$^+$ 324 b) 6-(p-nitrobenzyl)-1,4,8,11 - tetraazaundecane 30 ml 1M BH$_3$, THF solution is added to 480 mg 6-(4-nitrobenzyl) -1,4,8,11- tetraaza-5,7-dioxo-undecane at room temperature and the mixture is heated at reflux for 60 hours. Excess of diborane is destroyed by adding carefully dropwise abs. CH$_3$OH to the yellow solution cooled to 0°. The reaction mixture is concentrated several times with CH$_3$OH. The residue is suspended in abs. ethanol using an ultrasonic bath and then filtered. Gaseous HCl is passed through the yellow filtrate for 20 min. The resulting precipitate is purified on a silica gel column with CHCl$_3$/CH$_3$OH/25%NH$_4$OH 5:5:2. To obtain the chlorhydrate, gaseous HCl is passed through the ethanolic solution of the purified amine.

Rf: 0.36(SiO$_2$ CHCl$_3$/CH$_3$OH/25%NH$_4$OH 5:5:2) MS (FAB) m/z relative intensity: 296 (MH$^+$,100)

c) Fmoc-6-(p-nitrobenzyl)-1,4,8,11-tetraazaundecane 750 mg 6-(p-nitrobenzyl)-1,4,8,11-tetraazundecane, 4HCl are suspended at room temperature in 45 ml dioxane and 15 ml H$_2$O. 5730 mg 9-fluorenylmethyl-succinimidyl carbonate and 1430 mg sodium bicarbonate are added thereto. After stirring for 2 hours at room temperature, the colourless suspension is adjusted to pH4 with 2N HCl, and then lyophilized. The colourless solid is chromatographied on silica gel with CHCl$_3$. The resulting substance is lyophilized.

Rf: 0.30 (SiO$_2$ CHCl$_3$/CH$_3$OH 100:1) MS(FAB) m/z (relative intensity) 1184(M$^+$,73), 962(MH$^+$-Fmoc, 100)

d) Fmoc-6-(p-aminobenzyl)-1,4,8,11-tetraazaundecane 910 mg of the compound c) are dissolved in 10 ml isopropyl acetate and diluted with 60 ml CH$_3$OH. Water is added dropwise to this solution until it becomes turbid (about 4 ml). 200 mg Pd on activated Al$_2$O$_3$ (5% Pd) are added under argon atmosphere and the suspension is deaerated with H$_2$. Hydrogenation is performed for 1 hour at 760 mm Hg. The suspension is then filtered on Hyflo, the filtrate is concentrated, the oily residue is taken up in dioxane/H$_2$O and lyophilized. After purification by chromatography on silica gel with CHCl$_3$, the product is taken up in dioxane and lyophilized.

Rf: 0.13 (SiO$_2$, CHCl$_3$/CH$_3$OH 100:1) MS(FAB) m/z (relative intensity): 1154(M$^+$,35), 932(MH$^+$-Fmoc, 100).

e) Fmoc-6-(p-isothiocyanatobenzyl)-1,4,8,11-tetraazaundecane 460 μl thiophosgen are added at room temperature to a 2-phase mixture of 640 mg compound d) in 4 ml CCl$_4$ and 4 ml 3N HCl. The orange mixture is stirred for 1 hour at room temperature. After distillation under high vacuo of the solvent, the oily residue is taken up in dioxane/water and lyophilized. The resulting pale yellow solid can be used without further purification.

Rf: 0.29 (SiO$_2$, CHCl$_3$/CH$_3$OH 100:2) MS(FAB) m/z relative intensity: 1196 (M$^+$,100), 974(MH$^+$-Fmoc, 84)

EXAMPLE 2

$^{99m}$Tc Labelled Compound of Example 1

To 1 ml generator eluate of $^{99m}$TcO$_4$Na (eluted after 3 hours) in physiological saline having a radioactivity of 30–45 mCi there is added 1 ml tartarate solution (2.09×10$^{-5}$ mol; pH=7) previously deaerated with a nitrogen stream, and 10 μl SnCl$_2$, 2 H$_2$O (1.49×10$^{-8}$ mol) in 0.1N HCl. 50 μg of the Example 1 compound are then added and the resulting mixture is stirred. If desired, the chelate may be purified on a PRP-1 Hamilton column (organic polymers).

EXAMPLE 3 b) Cleavage of the Fmoc-group on Lys:
100 mg of the compound of step a) are treated with 10 ml DMF/piperidine 4/1 at room temperature for 30 minutes. Subsequent removal of the solvent (high vacuo) and purification on silica gel using chloroform/methanol/50% AcOH 8/2/0.25→7/4/2 yields pure and homogenous N,N,N',N",N"'-pentakis(tert.-butyl-carboxymethyl) -1-[(4-amido-succinyl-DPhe$^1$-Tyr$^3$-ε-Fmoc-Lys$^5$-octreotide)benzyl]-diethylenetriamine.

c) Removal of the tert.-butyl-groups:
30 mg of the endproduct of step b) are suspended in 3 ml methylene chloride. After treatment with 3 ml ethanedithiol under inert atmosphere (argon) 3 ml trifluoroacetic acid/water 95/5 are added. After 24 hours at room temperature, the raw title compound is precipitated by adding 100 ml diethyl ether/3N HCl. The material is collected by filtration, purified and desalted on RP$_{18}$-HPLC using a water/acetonitrile/TFA (buffer A: 100/0 0.1% TFA and B: 200/800 0.1% TFA) buffer system (5→95% B in 20 min.), thus yielding the title compound.

$[\alpha]_D^{20}$=–17° (c=1.0, solvent 95% AcOH) MH$^+$: 1615

The starting materials are prepared as follows:

d) ε-Fmoc-Lys$^5$-Tyr$^3$-octreotide:
5 g Tyr$^3$-octreotide acetate are dissolved in 200 ml of DMF/water (3/1) and after addition of 5 g sodium bicarbonate, 1.6 g fluorenemethyloxycarbonyl-hydroxysuccinimidester (FmocHOSu) are added thereto. After one hour reaction time under thin layer chromatography control (solvent system chloroform/methanol/AcOH 8/2/0.25) the reaction mixture is diluted with 800 ml 0.1N NaOH solution and extracted with ethyl acetate/methanol 9/1. The organic phase is dried with sodium sulfate and evaporated under reduced pressure.

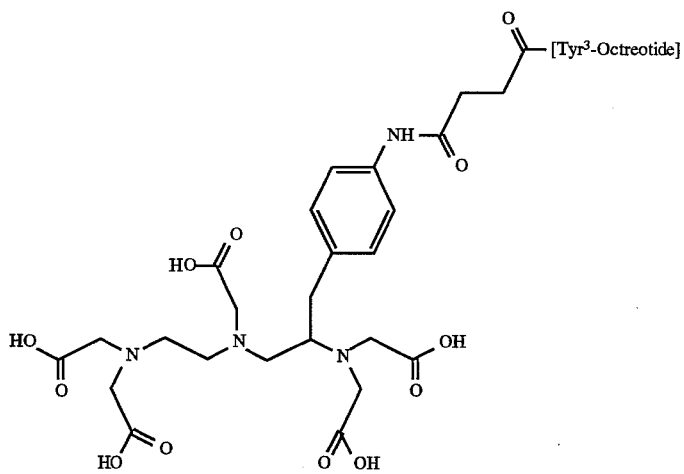

a) 150 mg Succinyl-DPhe$^1$-ε-Fmoc-Lys$^5$-Tyr$^3$-octreotide, 100 mg N,N,N',N",N"'-pentakis(tert.-butyl-carboxymethyl)-1-[(4-aminophenyl)methyl]-diethylenetriamine, 35 mg DCCI and 27 mg HOBT are dissolved in 20 ml DMF. After 16 hours at room temperature the solvent is removed by evaporation under reduced pressure. Purification on silica gel 60 using chloroform/methanol/50% AcOH 8/2/0.25 yields N,N,N',N",N"'-pentakis(tert.-butyl-carboxymethyl)-1-[(4-amido-succinyl-DPhe$^1$-Tyr$^3$-ε-Fmoc-Lys$^5$-octreotide)benzyl]-diethylenetriamine in pure form.

Purification is achieved using silica gel 60 (Merck 9385) as stationary phase and methylene chloride/methanol (9/10) as eluent. Fractions with a purity grade higher than 95% (TLC control) are collected and the solvent is removed by evaporation.

$[\alpha]_D^{20}$ = –18.7° (c = 0.5, solvent 95% AcOH)

e) Succinyl-DPhe[1]-ε-Fmoc-Lys[5]-Tyr[3]-octreotide:

600 mg ε-Fmoc-Tyr[3]-octreotide are dissolved in 100 ml of a mixture of water/dioxane 3/2 containing 1 ml triethylamine. After addition of 100 mg succinic anhydride the reaction mixture is kept at room temperature for 3 to 4 hours. Isolation of the title compound is achieved by freeze drying and by subsequent purification on a silica gel column using chloroform/methanol/50%AcOH 9/1/0.125 as eluent.

$[\alpha]_D^{20} = -34°$ (c = 0.25, solvent 95% AcOH)

By repeating the procedure of Example 3 but using the appropriate starting materials, the following compounds may be prepared:

EXAMPLE 4

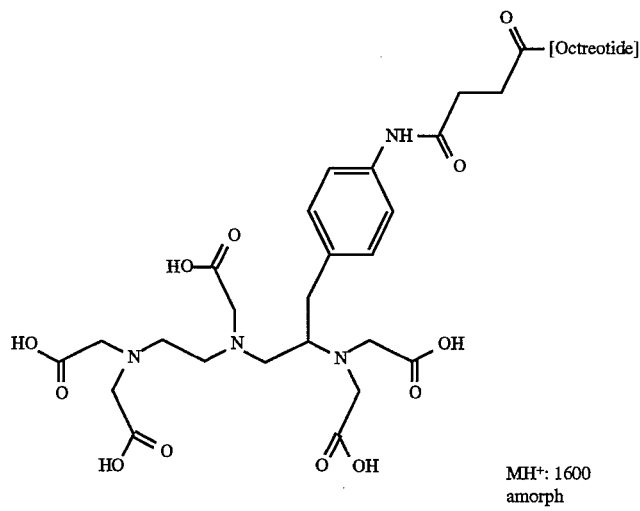

MH+: 1600
amorph

EXAMPLE 5

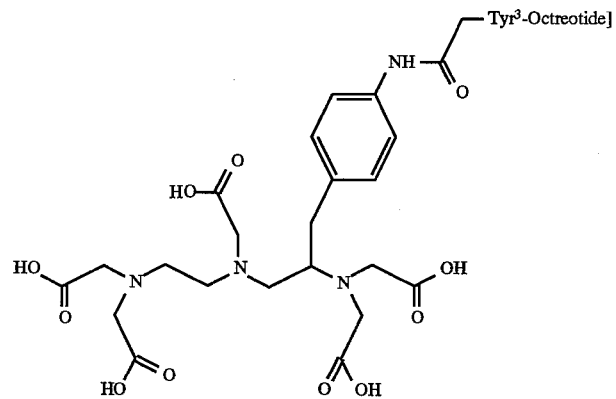

$[\alpha]_D^{20} = -14.2°$ (c = 0.58, solvent 95% AcOH) MH+: 1573

EXAMPLE 6

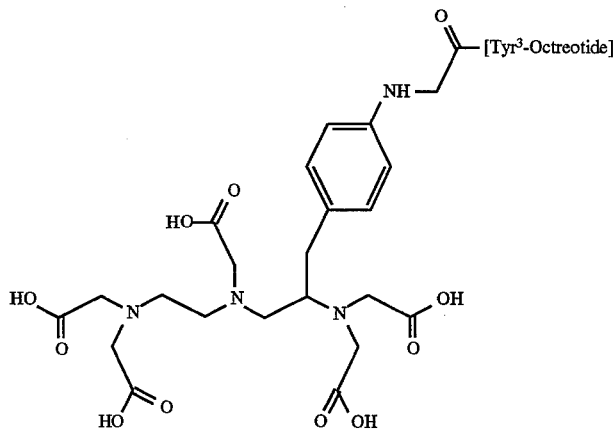

$[\alpha]_D^{20} = -10°$ (c = 0.25, solvent 95% AcOH) MH⁺: 1573

EXAMPLE 7

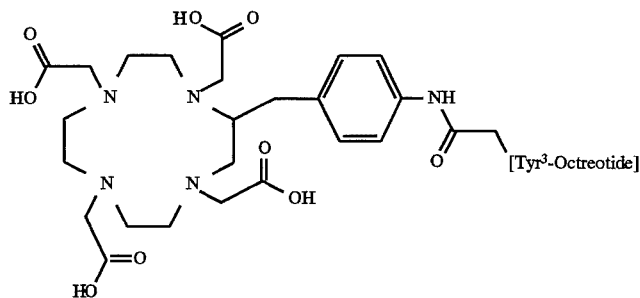

MH⁺ 1585.

EXAMPLE 8

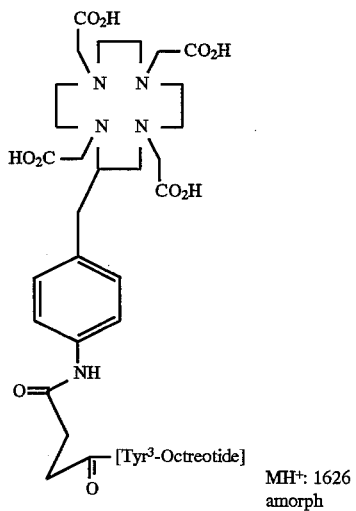

MH⁺: 1626
amorph

Glyoxyl-DPhe¹-ε-Fmoc-Lys⁵-Tyr³-octreotide used as starting material in Example 5 may be prepared as follows:

620 mg of ε-Fmoc-Lys⁵-Tyr³-octreotide are dissolved in 50 ml of a mixture water/dioxane 1/3. After addition of 70 mg glyoxylic acid and 41 mg NaCNBH₃, the reaction mixture is adjusted to pH 5 with 0.1N HCl and kept at room temperature over night. Isolation of the title compound is achieved by freeze drying and by subsequent purification on a silica gel column using chloroform/methanol/50% AcOH 8/2/0.25→7/3/1 as eluent.

$[\alpha]_D^{20} = -42°$ (c = 0.5, solvent 95% AcOH)

N,N,N',N'',N''-pentakis-tert.-butyl-carboxymethyl-1-(4-aminocarboxymethyl-benzyl)-diethylenetriamine used as starting material in Example 6 may be prepared as follows:
 700 mg N,N,N',N'',N''-pentakis-tert.-butyl-carboxymethyl-1-(4-aminobenzyl)-diethylenetriamine are dissolved in 25 ml in a mixture of water/dioxane 1/2. After addition of 103 mg of glyoxylic acid monohydrate and 64 mg NaCNBH₃, the reaction mixture is adjusted to pH 5 with 0.1N HCl and kept at room temperature for 5 hours. Isolation of the title compound is achieved by freeze drying and by subsequent purification on a silica gel column using chloroform/methanol/50% AcOH 9/1/0.125→8/2/0.25 as eluent.

EXAMPLE 9

$^{111}$In Labeled Compound of Example 3

8.6 μl of $^{111}$InCl$_3$ (21 mCi/ml, 0.01–0.03 M HCl) and 2 μl of 0.1M NaOH is added to 10 μl of 0.1M NaOAc (pH 4.0). 1 μl of the LIGAND (100 μM compound of Example 3 in 0.1M NaOAc pH 4.0) is added. The solution obtained is left at ambient for between three and thirty minutes for complete complexation. An aliquot is removed for a HPLC quality control run to ascertain the levels of $^{111}$In complexed to the conjugate and that present as the acetate complex. The HPLC analysis is performed on a μbondapak® (Registered Trademark, Waters) C18 column (3.4×300 mm) using an eluant system of 20 mM NH$_4$OAc (pH 4.0) and a linear 0→60% MeCN gradient at 1.2 ml/min. Generally the elution profile shows free $^{111}$In eluting with the solvent front and the radio labeled conjugate eluting at 9–11 mins. The radiochemical purity is typically >99.5%.

EXAMPLE 10

$^{88}$Y Labeled Compound of Example 3

The $^{88}$Y labeled CHELATE is prepared by adding evaporating to dryness under filtered air 0.02 ml of $^{88}$Y (5 mCi/ml, 6M HCl). The residue obtained is dissolved in 20 μl of 0.1M NaOAc (pH 4.0) and 4.0 μl of 100 μM compound of Example 3 (0.1M NaOAc pH 4.0) added. The solution is left at ambient for between three and 15 minutes for complete complexation. An aliquot is removed for a HPLC quality control run to ascertain the levels of $^{88}$Y complexed to the conjugate and that present as the acetate complex, as disclosed in Example 6. The radiochemical purity is typically >99.5%.

EXAMPLE 11

$^{90}$Y Labeled Compound of Example 3

The $^{90}$Y labeled CHELATE is prepared by adding 1 μl of $^{90}$Y (0.16 mCi, 0.01M HCl) to 11 μl of 9 μM compound of Example 3 (0.1M NH$_4$OAc pH 5.0). This solution is incubated at room temperature for 3 mins before use. An aliquot is removed for a HPLC quality control run to ascertain the levels of $^{90}$Y complexed to the conjugate and that present as the acetate complex, as disclosed in Example 9. The radiochemical purity is typically 99.5%.

The labelling procedures of Examples 9, 10 and 11 may be repeated using as ligands the compounds of Examples 4 to 6 above, thus yielding the corresponding $^{111}$In, $^{88}$Y and $^{90}$Y chelates.

EXAMPLE 12

$^{90}$Y Labelled Compound of Example 7

The $^{90}$Y labelled CHELATE is prepared by adding 10 μl of $^{90}$Y (0.6 mCi, 0.04M HCl) to 12 μl of 20 μM compound of Example 7 (0.1M NMe$_4$OAc, 0.1% BSA, pH 6.0). This solution is heated for 15 minutes at 90° before use. An aliquot is removed and diluted in 0.1M DTPA (pH 6.0) prior to HPLC quality control to ascertain the levels of $^{90}$Y incorporated into the conjugate. The radiolabelled purity is typically >99.5% and the radiolabelled compound is stable, e.g. for up to 6 days at 4°.

By following the procedure of Example 12 above, the $^{90}$Y complex of compound of Example 8 may be prepared.

We claim:

1. A compound of formula I

X—NH—P wherein X is a radical selected from
a) a chelating group of formula X$_1$

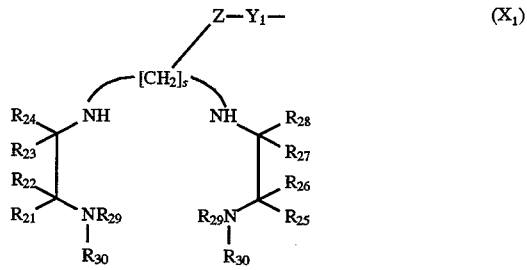

wherein each of $R_{21}$ to $R_{28}$ independently is hydrogen, $C_{1-6}$alkyl or hydroxy substituted $C_{1-6}$alkyl, one of $R_{29}$ and $R_{30}$ is hydrogen, $C_{1-6}$alkyl or an amino protecting group and the other is hydrogen or $C_{1-4}$alkyl s is 2, 3 or 4, Z is a divalent group, and Y$_1$ is a single bond or a spacer group, and b) a radical of formula X$_2$

[R$_1$]—CH$_2$—R$_2$—NH—Y$_2$—   (X$_2$)

wherein

R$_1$ is a bifunctional chelating group derived from a polyamino-polycarboxylic acid or anhydride and bearing the moiety —CH$_2$—R$_2$—NH—Y$_2$ on a tertiary carbon atom, R$_2$ is C$_{1-3}$alkylene or optionally substituted phenylene, and Y$_2$ is —CO— or a spacer group comprising on one end a —CO— and on the other end a —CH$_2$— group or a —CO— at each end, P—NH— is the N-terminal residue of a somatostatin peptide of formula P—NH$_2$ in free form, in salt form or in a complexed form with a nuclide.

2. A compound according to claim 1 wherein P—NH— is a residue of formula (a)

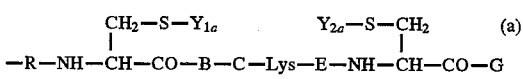

wherein

R is
a) an L- or D-phenylalanine residue optionally ring-substituted by F, Cl, Br, NO$_2$, NH$_2$, OH, C$_{1-3}$alkyl and/or C$_{1-3}$alkoxy;
b) the residue of a natural or non natural α-amino acid other than defined under a) above or of a corresponding D-amino acid, or
c) a dipeptide residue in which the individual amino acid residues are the same or different and are selected from those defined under a) and/or b) above, Y$_{1a}$ and Y$_{2a}$ represent together a direct bond or each of Y$_{1a}$ and Y$_{2a}$ is independently hydrogen, B is -Phe- optionally ring-substituted by halogen, NO$_2$, NH$_2$, OH, C$_{1-3}$alkyl and/or C$_{1-3}$alkoxy, or β-naphthyl-Ala C is (L)-Trp- or (D)-Trp- optionally α-N-methylated and optionally benzene-ring-substituted by halogen, $NO_2$, $NH_2$, OH, $C_{1-3}$alkyl and/or $C_{1-3}$ alkoxy, E is Thr, Ser, Val, Phe, Ile or an aminoisobutyric or aminobutyric acid residue G is a group of formula $$-COOR_7, -CH_2OR_{10}, -CON\begin{matrix}R_{11}\\R_{12}\end{matrix} \text{ or}$$

$$-CO-N\underset{\phantom{X_3}}{\overset{R_{16}}{\diagdown}}X_3$$

wherein $R_7$ is hydrogen or $C_{1-3}$alkyl, $R_{10}$ is hydrogen or the residue of a physiologically acceptable, physiologically hydrolysable ester, $R_{11}$ is hydrogen, $C_{1-3}$alkyl, phenyl or $C_{7-10}$phenylalkyl, $R_{12}$ is hydrogen, $C_{1-3}$alkyl or a group of formula —CH($R_{13}$)—$X_3$, $R_{13}$ is the substituent attached to the α-carbon atom of a natural or non natural α-amino acid and $X_3$ is a group of formula —$COOR_7$, —$CH_2OR_{10}$ or $$-CO-N\begin{matrix}R_{14}\\R_{15}\end{matrix}$$

wherein $R_7$ and $R_{10}$ have the meanings given above, $R_{14}$ is hydrogen or $C_{1-3}$alkyl and $R_{15}$ is hydrogen, $C_{1-3}$alkyl, phenyl or $C_{7-10}$phenylalkyl, and $R_{16}$ is hydrogen or hydroxy, with the proviso that when $R_{12}$ is —CH($R_{13}$)—$X_3$ then $R_{11}$ is hydrogen or methyl, wherein the residues B and E have the L-configuration, and the residues in the 2-and 7-position have the (L)- or (D)-configuration.

3. A compound according to claim 2 wherein G is a group of formula $$-CO-N\begin{matrix}R_{11}\\CH(R_{13})-X_3\end{matrix} \text{ wherein } X_3 \text{ is } -CO-N\begin{matrix}R_{14}\\R_{15}\end{matrix}$$

or —$CH_2OR_{10}$ and $R_{13}$ is —$CH_2OH$, —$(CH_2)_2$—OH, —$(CH_2)_3$—OH, —$CH(CH_3)OH$, isobutyl, butyl, naphthylmethyl or indol-3-yl-methyl.

4. A compound according to claim 1 wherein X is $X_2$ and $Y_2$ is —$COCH_2$—, —$CO(CH_2)_2$—, —$CH_2CO$—, —$(CH_2)_2$—CO— or a radical of formula (b')

$$-CO-R_5-CO- \qquad (b')$$

wherein $R_5$ is $C_{1-6}$alkylene optionally interrupted by one or more heteroatoms or radicals selected from oxygen, sulfur, CO, —NHCO—, N($C_{1-4}$alkyl)—CO—, —NH— and —N($C_{1-4}$alkyl)—; hydroxy substituted $C_{1-6}$alkylene; $C_{2-6}$alkenylene; optionally substituted cycloalkylene;

$$-\underset{R_6}{\overset{\phantom{|}}{C}H}-;$$

or a radical of formula ($α_1$)

$$-(CH_2)_{m'}-\underset{\phantom{A}}{\boxed{A}}-(CH_2)_{n'}- \qquad (α_1)$$

wherein each of m' and n' independently is 0, 1, 2 or 3, the ring A is optionally substituted and $R_6$ is a residue as attached to the α carbon atom of a natural or non natural α-amino acid.

5. A compound according to claim 1 which is complexed with a α-, β-, γ- or positron-emitting nuclide or a nuclide with Auger-e⁻-cascades.

6. A compound according to claim 5 wherein X is $X_2$ and the nuclide is selected from $^{111}$In, $^{90}$Y, $^{161}$Tb, $^{169}$Er, $^{140}$La, $^{212}$Bi, $^{153}$Sm, $^{64}$Cu, $^{67}$Cu, $^{211}$At, $^{111}$Ag, $^{32}$P, $^{51}$Cr, $^{67}$Ga, $^{71}$Ge and $^{169}$Yb.

7. A pharmaceutical composition comprising a compound of formula I according to claim 1, in free form or in pharmaceutically acceptable salt form or in a complexed form with a nuclide, in association with a pharmaceutically acceptable carrier or diluent.

8. A compound according to claim 1 in pharmaceutically acceptable salt form.

9. A compound according to claim 1 wherein $[R_1]\!-\!CH_2\!-\!R_2NH\!-$ is $Y_2$ is —CO—$CH_2$—, —CO—$(CH_2)_2$—, —$CH_2$—CO—, —$(CH_2)_2$—CO—, or —CO—$CH_2CH_2$—CO—, and —NH—P is a residue of the formula

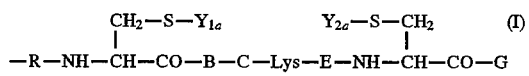

wherein

R is
a) L- or D-Phe or L- or D-Tyr; or
b) the residue of a natural or a synthetic α-amino acid having a side chain selected from alkyl of 3 to 7 carbon atoms, naphthylmethyl, pyridylmethyl, and indol-3-ylmethyl or a corresponding D-amino acid;

B is Phe, Tyr or 3-(2-naphthyl)alanine;

C is (D)-Trp;

E is Ser, Val, or Thr;

G is a group of formula

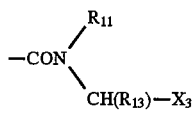

wherein $R_{11}$ hydrogen or $CH_3$, $R_{13}$ is —$CH_2OH$, —$(CH_2)_2$—OH, —$(CH_2)_3$—OH, —$CH(CH_3)$—OH, isobutyl, butyl, naphthylmethyl, or indol-3-ylmethyl;

$X_3$ is a group of formula —$CH_2$—$OR_{10}$ or —CO—$NR_{14}R_{15}$, wherein $R_{10}$ is hydrogen or a physiologically acceptable, physiologically hydrolyzable ester residue;

$R_{14}$ is hydrogen or $C_{1-3}$alkyl;

$R_{15}$ is hydrogen, $C_{1-3}$alkyl, phenyl or $C_{7-10}$phenylalkyl; and $Y_{1a}$ and $Y_{2a}$ together are a direct bond;

wherein the residues B and E have the L-configuration, and the residues in the 2-and 7-position independently have the (L)- or (D)-configuration; in free form or in pharmaceutically acceptable salt form or in complexed form with a nuclide.

10. A compound according to claim 9 wherein

R is L- or D-Phe, L- or D-Trp or L- or D-3-(2-naphthyl)alanine; or

B is Phe, Tyr or 3- (2-naphthyl)alanine;

C is (D)-Trp;

E is Val or Thr;

G is a group of formula

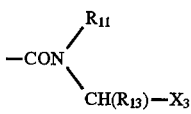

wherein $R_{11}$ hydrogen, $R_{13}$ is —$CH_2OH$, —$CH(CH_3)OH$, 3-(2-naphthyl)alanine, or indol-3ylmethyl;

$X_3$ is a group of formula —$CH_2OH$ or —$CONH_2$, and $Y_{1a}$ and $Y_{2a}$ together are a direct bond.

11. A compound of the formula

X—NH—P  I wherein

X is a chelating group of the formula

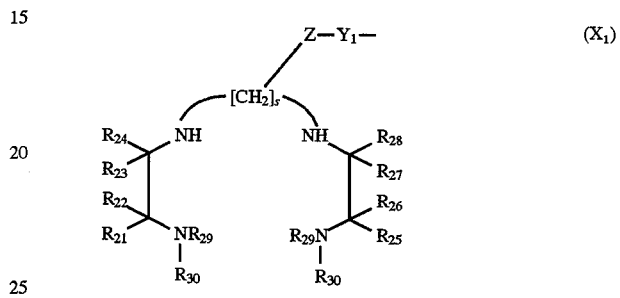

wherein each of $R_{21}$ to $R_{28}$ is independently hydrogen, $C_{1-6}$alkyl or hydroxy substituted $C_{1-6}$alkyl;

one of $R_{29}$ and $R_{30}$ is hydrogen, $C_{1-6}$alkyl or an amino protecting group and the other is hydrogen or $C_{1-4}$alkyl;

s is 2, 3, or 4;

Z is a divalent group;

$Y_1$ is a single bond or a spacer group, and

—NH—P is the N-terminal residue of a somatostatin peptide of formula $H_2N$—P, in free form or in pharmaceutically acceptable salt form or in complexed form with a nuclide.

12. A compound according to claim 11 wherein $Y_1$ is a single bond.

13. A compound according to claim 11 wherein the compound is complexed with a nuclide selected from Tc, Rh, Cu, Co and Re.

14. The compound according to claim 10 which is 6-(p-isothiocyanatobenzyl)-1,4,8,11-tetraazaundecyl-DPhe-Cys-Phe-DTrp-Lys-Thr-Cys-Thr-ol in free form or in pharmaceutically acceptable salt form or in complexed form with a nuclide.

15. The compound according to claim 14 which is $^{99m}Tc$ labelled 6-(p-isothiocyanatobenzyl)-1,4,8,11-tetraazaundecyl-DPhe-Cys-Phe-DTrp-Lys-Thr-Cys-Thr-ol in free form or in pharmaceutically acceptable salt form.

16. The compound according to claim 9 of the formula

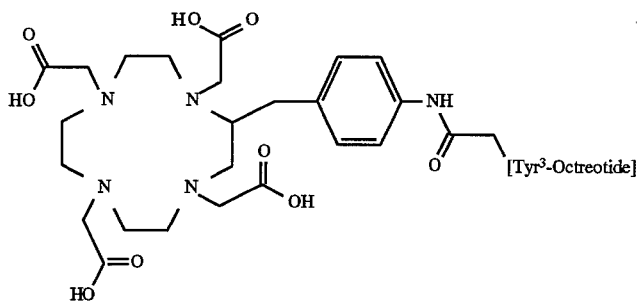

in free form or in pharmaceutically acceptable salt form or in complexed form with a nuclide.

17. The $^{90}$Y labelled compound of claim 16.

18. A compound according to claim 9 in which
—$Y_2$—NH—P is
a) —CO—CH$_2$—CH$_2$—CO—[Tyr$^3$-octreotide],
b) —CO—CH$_2$—CH$_2$—CO-octreotide,
c) —CO—CH$_2$—[Tyr$^3$-octreotide], or
d) —CH$_2$—CO—[Tyr$^3$-octreotide], and
[$R_1$]—CH$_2$—$R_2$—NH— is

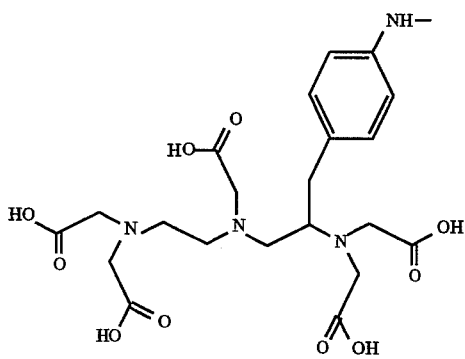

in free form or in pharmaceutically acceptable salt form or in complexed form with a nuclide.

19. A $^{90}$Y labelled compound of claim 18.

20. The compound according to claim 9 in which
—$Y_2$—NH—P is —CO—CH$_2$—CH$_2$—CO—[Tyr$^3$-octreotide] and
[$R_1$]—CH$_2$—$R_2$—NH— is

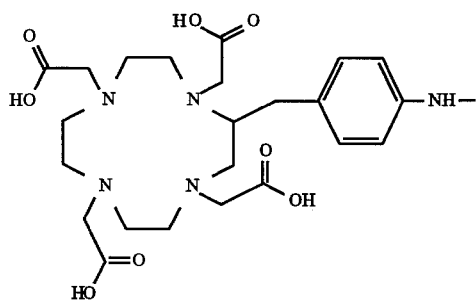

in free form or in pharmaceutically acceptable salt form or in complexed form with a nuclide.

21. The $^{90}$Y labelled compound of claim 20.

* * * * *